United States Patent [19]

Menzl et al.

[11] 4,151,164
[45] Apr. 24, 1979

[54] PROCESS FOR PREPARING 3-METHOXY-4-(4'-AMINOBENZENESUL-FONAMIDO)-1,2,5-THIADIAZOLE

[75] Inventors: Kurt Menzl; Rudolf Franzmair, both of Linz, Austria

[73] Assignee: Chemie Linz Aktiengesellschaft, Linz, Austria

[21] Appl. No.: 868,423

[22] Filed: Jan. 10, 1978

[30] Foreign Application Priority Data

Jan. 17, 1977 [DE] Fed. Rep. of Germany ....... 2701632

[51] Int. Cl.$^2$ .......................................... C07D 285/10
[52] U.S. Cl. .............................................. 260/239.95
[58] Field of Search ................... 260/239.95, 306.8 D

[56] References Cited

U.S. PATENT DOCUMENTS

| | | | |
|---|---|---|---|
| 3,247,193 | 4/1966 | Menzl | 260/239.95 |
| 3,467,653 | 9/1969 | Weinstock et al. | 260/239.95 |
| 3,636,209 | 1/1972 | Weinstock et al. | 424/229 |
| 3,812,182 | 5/1974 | Weinstock et al. | 260/239.95 |

FOREIGN PATENT DOCUMENTS 294081  11/1971  Austria .............................. 260/239.95

OTHER PUBLICATIONS

Parker, Quarterly Reviews, vol. 16, pp. 176–187 (1962).

*Primary Examiner*—Alton D. Rollins
*Attorney, Agent, or Firm*—Wenderoth, Lind & Ponack

[57] ABSTRACT

3-Methoxy-4-(4'-aminobenzenesulphonamido)-1,2,5-thiadiazole is prepared by reaction of 3-methoxy-4-chloro-1,2,5-thiadiazole with sulfanilamide in dimethylsulfoxide as solvent and in the presence of alkali hydroxides or carbonates using a reaction temperature of from ambient temperature to 95° C., whereby per mole of thiadiazole-compound from 1.2 to 1.5 mole of sulfanilamide and from 1.5 to 3 moles of the alkali hydroxide or carbonate are used, whereafter the reaction product is obtained by acidification.

2 Claims, No Drawings

PROCESS FOR PREPARING 3-METHOXY-4-(4'-AMINOBENZENESULFONAMIDO)-1,2,5-THIADIAZOLE

From U.S. Pat. No. 3,247,193 of one of the inventors 3-methoxy-4-(4'-aminobenzenesulfonamido)-1,2,5-thiadiazole is known to be a sulfonamide with good antibacterial properties, which penetrates easily the bloodtissular barriers so that high concentrations can be observed in organs such as the eyes.

According to U.S. Pat. No. 3,247,193, this sulfonamide is produced by reacting 3-halogen-4-amino-1,2,5-thiadiazole with N4-acylated sulfanilic acid chloride, whereafter the halogen was replaced by the methoxy group. However, this process is relatively expensive since the 3-halogen-4-amino-1,2,5-thiadiazoles used as starting material must be prepared by cleavage of diketothiapurines.

U.S. Pat. No. 3,636,209 has shown that 3-alkoxy-4-(4'-aminobenzenesulfonamido)-1,2,5-thiadiazoles with at least two C-atoms in the alkoxy group can also be obtained by reacting 3-alkoxy-4-chloro-1,2,5-thiadiazoles with sulfanilamide if 1.5-5 moles sulfanilamide are used per mole of 3-chloro-4-alkoxy-1,2,5-thiadiazole and at least a molar equivalent of an acid binding agent per mole of sulfanilamide is present, whereby amides, particularly acetamide, are used as solvent and the reaction is carried out at temperatures of about 110°-175° C., especially 145° C.

Yields for the reaction of alkoxychlorothiadiazoles are not given, but this U.S.-Patent Specification indicates that the corresponding 3-allyloxy-4-sulfanilamido-1,2,5-thiadiazole can be obtained according to this process in a yield of approximately 50%.

In accordance with Austrian Patent Specification 294 081, the costly sulfanilamide excess required according to the above described process can be avoided by heating in dimethylformamide at temperatures of 115° to 160° C., and by removing the water formed during the reaction by the way of azeotropic distillation at the same time.

According to this process crude 3-methoxy-4-(4'-aminobenzene-sulfonamido)-1,2,5-thiadiazole can be obtained in a yield of 91.4% of theory. However, in contrast to the sulfonamides likewise obtainable by this method, it has an intensive yellow colour and in the chromatogram it shows several additional spots which can also be seen in the pure product according to that patent specification; furthermore the yellow coloration can only be reduced, but not eliminated. A product of this kind is not suitable for use in pharmaceutical preparations. Efforts to effect purification by recrystallization instead of reprecipitation either failed or led to very considerable drops in yield, and even then the product was not suitable. Surprisingly, it has now been found that good yields of 3-methoxy-4-(4'-aminobenzene-sulfonamido)-1,2,5-thiadiazole can be obtained in a purity being in accordance with the quality requirements for pharmaceutical purposes if the reaction is carried out in dimethyl sulfoxide as the solvent and at considerably lower temperatures than those hitherto proposed. The crude product thus obtained in yields of more than 90% is already so pure that the product, after further recrystallization, e.g. from a mixture of methanol and water, is of pharmaceutical purity, i.e. it exhibits no additional spots in the chromatogram and is completely white.

Accordingly the present invention provides in a process for preparing substantially pure 3-methoxy-4-(4'-aminobenzene-sulfonamido)-1,2,5-thiadiazole by reacting 3-methoxy-4-chloro-1,2,5-thiadiazole with sulfanilamide in the presence of acid binding agents in a solvent the improvement, which comprises reacting the thiadiazole compound with the sulfanilamide at a temperature of from ambient temperature up to 95° C. in dimethyl sulfoxide as the solvent and in the presence of hydroxide or a carbonate of sodium or potassium, using from 1.2 to 1.5 moles of sulfanilamide and from 1.5 to 3 molequivalents of the hydroxide or carbonate of sodium or potassium per mole of 3-methoxy-4-chloro-1,2,5-thiadiazole, whereafter the reaction product is obtained by acidification. By lowering the reaction temperature within the range according to the present invention the purity of the reaction product increases and higher yields are obtained, but higher temperatures permit a shorter reaction time. Thus for example, when carrying out the reaction at ambient temperature a reaction time of approximately 10 days is necessary, whereby a yield of crude product of about 97% and a yield of pure product of about 88% being achieved, whereas with a reaction temperature of 70° C. a reaction time of only 48 hours is required for obtaining a yield of crude product of more than 90% which however corresponds to a yield of pure product of approximately 78–80%. For economical reasons, operation in the medium temperature range in accordance with the invention is generally preferred, reaction temperatures of 40°–80° C. are particularly advantageous.

The presence of small quantities of water, per example a few parts percent, can be tolerated. Therefore it is not necessary to use particularly dry reagents. Elimination of water during the reaction per example by the way of azeotropic distillation is likewise unnecessary.

Suitable acid-binding agents are sodium hydroxide or potassium hydroxide, or sodium carbonate or potassium carbonate, potassium carbonate being particularly preferred. The quantity of sulfanilamide and potassium carbonate used is somewhat higher than the quantity used according to the process of Austrian Patent Specification 294 081, but should never be as high as the amount used according to U.S. Pat. No. 3,636,209. The relatively narrow ranges of chloromethoxythiadiazole:sulfanilamide:potassium carbonate i.e. 1:1.2–1.5:1.5–3 represent the optimum molar ratios which should be kept within these limits.

The reaction product obtained can be isolated in a simple manner. As a particular advantage of the described process in most of the cases it is not necessary to remove unreacted chloromethoxythiadiazole by steam distillation. The required 3-methoxy-4-(4'-aminobenzene-sulfonamido)-1,2,5-thiadiazole simply crystallizes after acidification to a pH below 3 and is isolated by suction.

Further purification is made by recrystallization from solvents such as ethyl acetate, ethanol-water, aqueous e.g. 75% isopropanol or aqueous e.g. 50% methanol. An addition of charcoal might be advantageous.

The colour of a 5% solution of a so obtained pure product in 1 N NaOH is compared with a colour standard at a thickness of approximately 10 cm. The colour standard is obtained by adding 1% hydrochloric acid to 0.05 ml of a 5% solution of $FeCl_3.6H_2O$ in 1% hydrochloric acid, to obtain a volume of 10 ml. A solution of the reaction product with the same colour or a weaker colour meets the colour requirements. To prepare thin-layer chromatogram (TLC), 3-methoxy-4-(4'-aminobenzenesulfonamido)-1,2,5-thiadiazole is dissolved in acetone. 20 μg are applied to silica gel plates (KG 60 HF); the eluent used is a mixture of chloroform:methanol:glacial acetic acid:water in a ratio of 90:8:0.5:0.5 respectively. A 1% solution of p-dimethylaminobenzaldehyde in 1 N sulfuric acid was used for spraying.

EXAMPLE 1

150.6 g of 3-methoxy-4-chloro-1,2,5-thiadiazole (1 mole) were suspended in 156.26 g of dimethyl sulfoxide (2 mole) and 258.31 g of sulfanilamide (1.5 mole) and 414.63 g of potassium carbonate (3 mole) were then added. The mixture was kept at 70° C. for 48 hours while stirring. 600 ml of water were then added, the mixture was cooled to ambient temperature and adjusted to pH 1.5 with concentrated hydrochloric acid. The precipitated crystallized material was filtered off, washed with water and dried. A yield of 271.1 g of crude 3-methoxy-4-(4'-aminobenzenesulfonamido)-1,2,5-thiadiazole (94.67% of theory), melting point 138°–146° C., was obtained.

After recrystallization from methanol/water 1:1, using charcoal, 225.5 g of pure product, melting point 149°–150° C., were obtained. The yield was 78.75% of theory.

In the thin-layer chromatogram the pure substance showed no additional spots and met the colour standard.

In contrast to this, a 3-methoxy-4-(4'-aminobenzolsulfonamido)-1,2,5-thiadiazole, obtained as pure product in accordance with Example 5 of Austrian Patent Specification No. 294,081, showed 7 additional spots in the thin-layer chromatogram. Its colour was stronger than a colour standard obtained by dissolving 6.4 ml of the 5% $FeCl_3.6H_2O$ solution in 1% HCl and filling up with 1% HCl to obtain a volume of 10 ml; it was thus approximately 128 times as much coloured as the product obtained according to the invention.

EXAMPLE 2

150.6 g of 3-methoxy-4-chloro-1,2,5-thiadiazole (1 mole) were suspended in 390.65 g (5 mole) of dimethyl sulfoxide, and 258.31 g of sulfanilamide (1.5 mole) and 414.63 g of potassium carbonate (3 mole) were added. The mixture was left to react for 10 days at temperatures of 28°–30° C., and was then worked up according to Example 1. 277.2 g of crude 3-methoxy-4-(4'-aminobenzenesulfonamido)-1,2,5-thiadiazole were obtained, corresponding to a yield of 96.82% of theory. Melting point: 144°–147° C.

After recrystallization from methanol/water 1:1 with charcoal pure 3-methoxy-4-(4'-aminobenzenesulfonamido)-1,2,5-thiadiazole, melting point 149°–150° C., was obtained in a yield of 251.4 g, i.e. 87.82% of theory, related to the amount of chloromethoxythiadiazole used. The product showed no additional spots in TLC and met the colour standard.

EXAMPLE 3

The mixture according to Example 2 was allowed to react for 237 hours at a temperature of 24° C. On completion of the reaction, 600 ml of water were added, and the mixture was brought to pH 1.5 at 60° C. by adding concentrated hydrochloric acid. After the crystalline substance so obtained had been filtered off, crude 3-methoxy-4-(4'-aminobenzene-sulfonamido)-1,2,5-thiadiazole, melting point 147°–150° C., was obtained in a yield of 258.0 g, i.e. 90.12% of theory. After recrystallization from 50% methanol with the addition of animal charcoal, pure 3-methoxy-4-(4'-aminobenzenesulfonamido)-1,2,5-thiadiazole, having a melting point of 149°–150° C. was obtained in a yield of 224.9 g, i.e. 78.56% of theory. The thin-layer chromatogram showed no additional spots and the product met the colour standard.

EXAMPLE 4

If the same mixture as described in Example 2 is allowed to react for 140 hours at 40° C., then using the procedure described in Example 1, crude 3-methoxy-4-(4'-aminobenzene-sulfonamido)-1,2,5-thiadiazole is obtained in a yield of 271.4 g i.e. 94.79% of theory. Melting point: 147°–149° C. After recrystallization from 50% methanol with animal charcoal added, pure 3-methoxy-4-(4'-aminobenzolsulfonamido)-1,2,5-thiadiazole having a melting point of 149°–150° C. was obtained in a yield of 222.5 g, i.e. 77.72% of theory.

EXAMPLE 5

150.6 g (1 mole) of 3-methoxy-4-chloro-1,2,5-thiadiazole were suspended in 156.26 g of dimethyl sulfoxide (2 mole). 258.81 g of sulfanilamide (1.5 mole) and 414.63 g of potassium carbonate (3 mole) were added thereto while stirring. The mixture was then heated for 8 hours on a steam bath, and was cooled slightly particularly at the beginning so as to keep the internal temperature at 91°–95° C. After completion of the reaction, the reaction mixture was mixed with 600 ml of water, and its pH was adjusted to 6 at 60° C. by adding concentrated hydrochloric acid. To remove any 3-methoxy-4-chloro-thiadiazole still present, steam distillation was carried out whereby 1 l of distillate was drawn off.

The remaining reaction mixture was then adjusted to pH 1.5 at 80° C. After cooling, the crystallized material obtained was separated and dried. 227.1 g of a slightly yellow 3-methoxy-4-(4'-aminobenzenesulfonamido)-1,2,5-thiadiazole having a melting point of 143°–149° C. were obtained, corresponding to a yield of 82.82% of theory. After recrystallization from 50% methanol, 168.4 g of pure product having a melting point of 149°–150° C. were obtained, the yield being 69.73% of theory. The product met requirements as regards the colour standard and the thin-layer chromatogram.

EXAMPLE 6

75.3 g of 3-methoxy-4-chloro-1,2,5-thiadiazole (0.5 mole), 103.32 g of sulfanilamide (0.6 mole) and 712.25 g of potassium carbonate (1.25 mole) were reacted in 78.13 g of dimethyl sulfoxide (1 mole) and were further treated as described in Example 1. 123.1 g of crude 3-methoxy-4-(4'-aminobenzene-sulfonamido)-1,2,5-thiadiazole (85.99% of theory) were obtained.

The mixture was recrystallized from methanol/water 1:1 using charcoal, as described in Example 1. 104.2 g of pure product (72.78% of theory) having a melting point of 149°–150° C. were obtained. The product showed no additional spots in TLC and met the colour standard.

EXAMPLE 7

75.3 g of 3-methoxy-4-chloro-1,2,5-thiadiazole (0.5 mole), 103.32 g of sulfanilamide (0.6 mole) and 207.31 g of potassium carbonate (1.5 mole) were reacted in 195.33 g of dimethysulfoxide (2.5 mole) and worked up as described in Example 2. 137.5 g of crude 3-methoxy-4-(4'-aminobenzene-sulfonamido)-1,2,5-thiadiazole (96.05% of theory) were obtained. The mixture was recrystallized from methanol/water 1:1 with charcoal added, as described in Example 2. 126.87 g of pure product (88.63% of theory) having a melting point of 149°–150° C. were obtained; the product showed no additional spots in TLC and met the colour standard.

What we claim is:

1. In a process for preparing substantially pure 3-methoxy-4-(4'-aminobenzenesulfonamido)-1,2,5-thiadiazole by reacting 3-methoxy-4-chloro-1,2,5-thiadiazole with sulfanilamide in the presence of acid binding agents in a solvent, the improvement which comprises reacting the thiadiazole compound with the sulfanilamide at a temperature of from ambient temperature up to 95° C. in dimethylsulfoxide as the solvent and in the presence of a hydroxide or a carbonate of sodium or potassium, using from 1.2 to 1.5 moles of sulfanilamide and from 1.5 to 3 moles of the hydroxide or carbonate of sodium or potassium per mole of 3-methoxy-4-chloro-1,2,5-thiadiazole, whereafter the reaction product is obtained by acidification followed by purification by recrystallization.

2. The process according to claim 1, in which the reaction is carried out at a temperature of 40°–80° C.

* * * * *